United States Patent [19]

Rao

[11] 4,085,202

[45] Apr. 18, 1978

[54] TESTOSTERONE DERIVATIVES

[75] Inventor: Pemmaraju Narasimha Rao, San Antonio, Tex.

[73] Assignee: Becton, Dickinson and Company, Rutherford, N.J.

[21] Appl. No.: 727,409

[22] Filed: Sep. 29, 1976

Related U.S. Application Data

[62] Division of Ser. No. 615,812, Sep. 22, 1975, Pat. No. 4,031,117.

[51] Int. Cl.$^2$ ..................... G01N 33/16; A61K 39/00
[52] U.S. Cl. ........................................ 424/1; 23/230 B; 260/112 R; 424/8
[58] Field of Search ..................... 424/118, 238, 242; 260/112 R, 239.55 C, 397, 397.1; 23/230 B

*Primary Examiner*—Benjamin R. Padgett
*Assistant Examiner*—Christine M. Nucker
*Attorney, Agent, or Firm*—Marn & Jangarathis

[57] ABSTRACT

Testosterone-15α or β-carboxyethyl thioether, 5α-, dihydrotestosterone-15α or β-carboxyethyl thioether related compounds and intermediates for preparation thereof. The compounds are conjugated to an immunological protein and employed to elicit an antibody highly specific to testosterone and 5α-dihydrotestosterone respectively. The elicited antibody can be employed for determination of testosterone and 5α-dihydrotestosterone respectively, in samples, by radioimmunoassay.

19 Claims, No Drawings

TESTOSTERONE DERIVATIVES

This is a division of application Ser. No. 615,812, filed Sept. 22, 1975, now U.S. Pat. No. 4,031,117.

The present invention relates to testosterone derivatives, intermediates and processes for the preparation thereof and uses therefor.

More particularly, the invention relates to the following final products:

R is an alkyl group of from 1 to 6 carbon atoms, preferably from 1 to 2 carbon atoms; and A is:
—OH
—OM wherein M is an alkali metal barium, calcium, or strontium
—OY wherein Y is an alkyl group of from 1 to 6 carbon atoms.

The compounds may be produced by the following sequence, employing as a representative example, the $\beta$ form of the testosterone final product (structural Compound I) wherein R is ethyl and A is —OH:

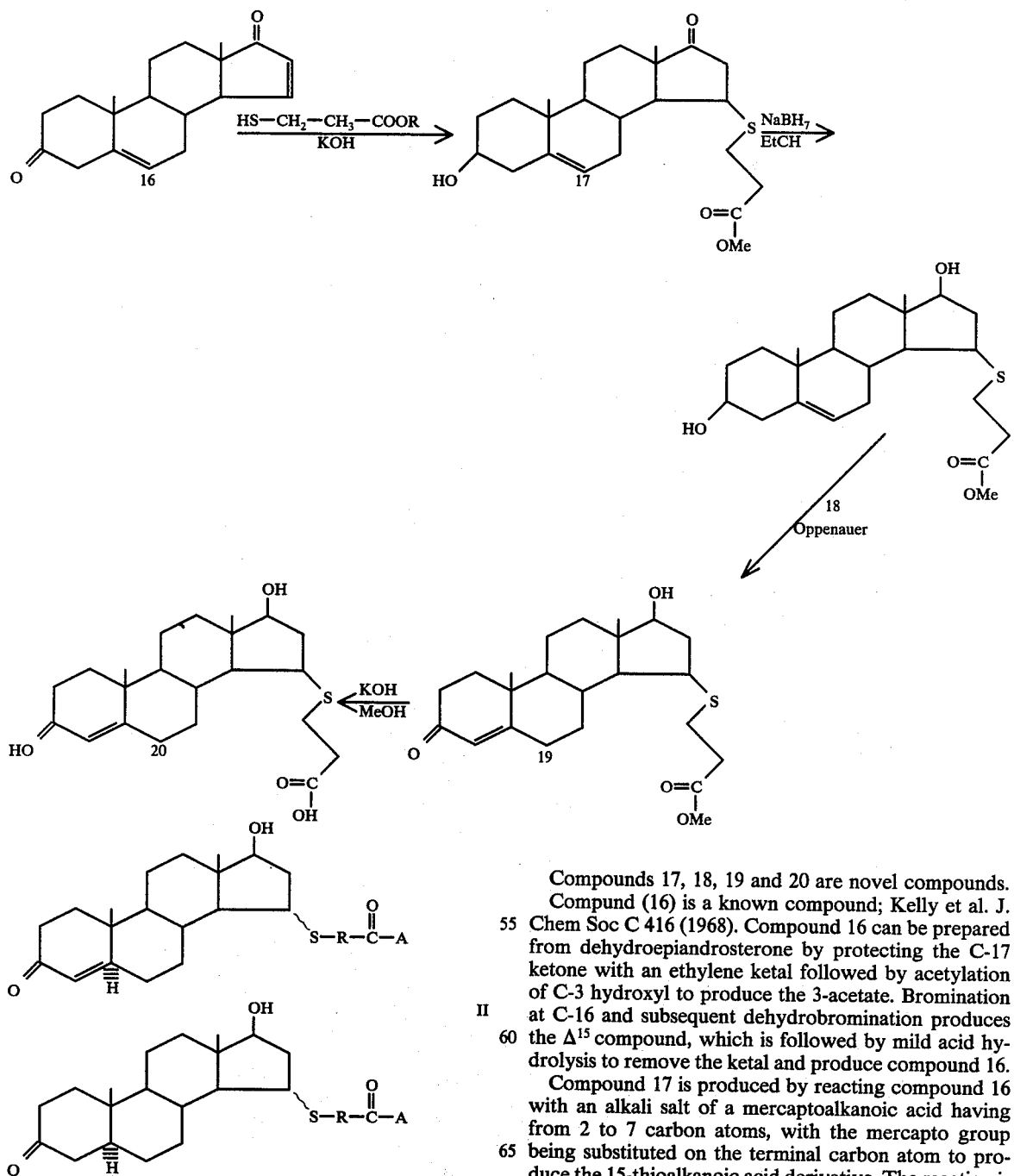

Compounds 17, 18, 19 and 20 are novel compounds.

Compund (16) is a known compound; Kelly et al. J. Chem Soc C 416 (1968). Compound 16 can be prepared from dehydroepiandrosterone by protecting the C-17 ketone with an ethylene ketal followed by acetylation of C-3 hydroxyl to produce the 3-acetate. Bromination at C-16 and subsequent dehydrobromination produces the $\Delta^{15}$ compound, which is followed by mild acid hydrolysis to remove the ketal and produce compound 16.

Compound 17 is produced by reacting compound 16 with an alkali salt of a mercaptoalkanoic acid having from 2 to 7 carbon atoms, with the mercapto group being substituted on the terminal carbon atom to produce the 15-thioalkanoic acid derivative. The reaction is generally effected at temperatures of from $-10°$ C to $100°$ C. The 15-thioalkanoic acid derivative is then eswherein terified, for example, with diazomethane, to produce compound 17.

Alternatively, the Δ[15]-compound 16 may be reacted with the methyl ester of mercaptoalkanoic acid in the presence of an organic base such as piperidine to give 17 in excellent yield.

The C-17 ketone group is then reduced to produce compound 18. The reduction can be effected by the use of a metal hydride which specifically reduces a ketone group, such as, sodium borohydride.

Compound 18 is then subjected to controlled Oppenauer oxidation to produce compound 19.

Compound 20 is produced by hydrolysis of compound 19.

The compound represented by structural formula II, in particular, 5α-di hydrotestosterone-15α or β-carboxyethyl thioether is produced by an analogous procedure employing isoandrosterone, instead of dehydroepiandrosterone, as the starting compound, as represented by the following sequence:

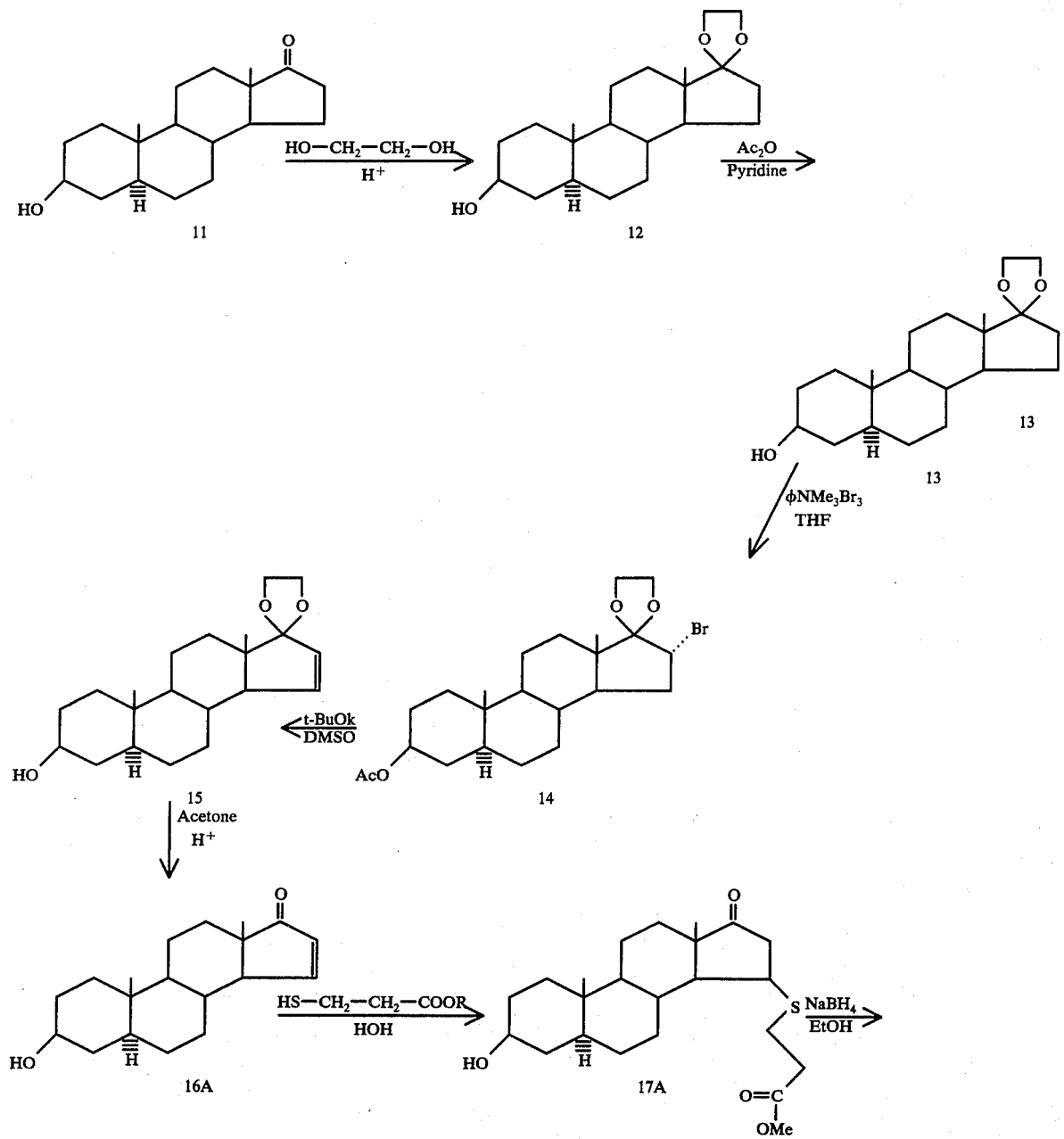

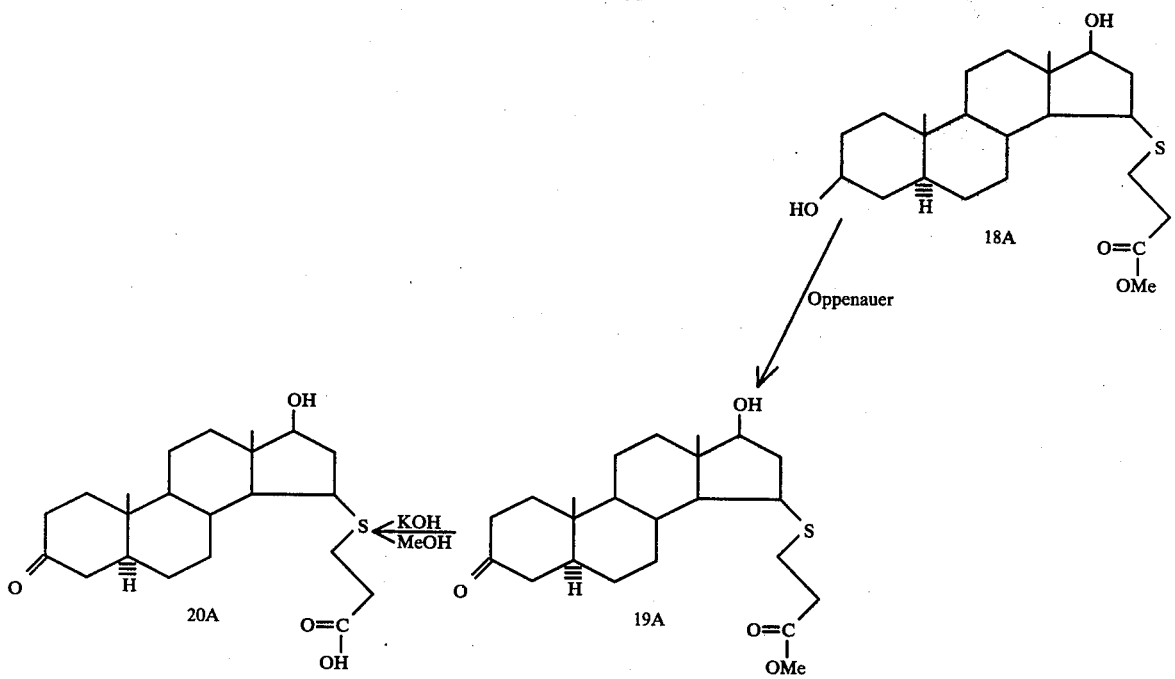

EXAMPLE I

3β-Hydroxyandrost-5-en-17-one-15β-carboxyethyl thioether methyl ester (17)

The Δ[15]-steroid (16, 8.05g) was dissolved in tetrahydrofuran (200 ml). A solution of potassium-3-mercaptopropionate (10.00g) in water (70 ml) and 5% KOH (7 ml) was added. The mixture was stirred under $N_2$ for 2½ hours, then diluted with water (600 ml), extracted with ether, and separated into neutral and acidic portions. The acidic portion was cooled and brought to pH 2 with HCl. Isolation with ethyl acetate and crystallization from acetone gave an acidic material: mp 196°-198° C; $\nu_{max}$3350, 1750, 1700 cm.$^{-1}$;

Calcd for $C_{22}H_{32}O_4S$: C., 67.31; H., 8.22; O., 16.30; S., 8.17. Found: C., 67.37; H., 8.34

This acidic material was dissolved in a minimum amount of methanol, cooled to 0° C, and treated with diazomethane. Crystallization from ether-hexane gave (17, 8.15g, 71.3%). mp 116°-118° C; $\nu_{max}$3440, 1740 cm.$^{-1}$;δ 1.03 (S.—CH₃), 1.07 (S.—CH₃), 2.72 (M.(—CH₂—), 3.52 (S.—OCH₃)ppm.

ANAL. Calcd for $C_{23}H_{34}O_4S$; C., 67.95; H., 8.43; O., 15.74; S., 7.89. Found: C., 67.83; H., 8.41.

The 15α forms of the above compounds can be produced by isomerizing the 15-β form of compound 17 or 17A with sodium hydroxide, followed by esterification with diazomethane to produce the 15α form of compound 17 or 17A.

The procedure for producing compounds 18, 19 and 20 (also 18A, 19A and 20A) in the 15α form is as previously described, starting with the 15α form of compound 17 or 17A.

The invention will be further described with respect to the following examples:

EXAMPLE II

3β-Hydroxyandrost-5-en-17-one-15β-methyl (propionate) thioether (17)

To a stirred solution of 3β-hydroxyandrost -5, 15-diene-17-one (16, 0.199g) in freshly-distilled tetrahydrofuran (5 ml) containing methyl- 3 - mercaptopropionate (0.15 ml), piperidine (3 drops) was added. The reaction mixture was stirred at room temperature under anhydrous conditions for 1 hour. The solution was diluted with ice-cold water (100 ml), neutralized with dilute hydrochloric acid and extracted with ethyl acetate. The ethyl acetate extract was washed with water, brine, and dried over anhydrous sodium sulfate. The solution was filtered and evaporated to dryness. The oily residue was crystallized from ethyl acetate-petroleum ether to give (17, 0.21 g) mp 118°-119°.

EXAMPLE III

3β,17β-Dihydroxyandrost-5-en-15β-methyl (pripionate) thioether (18)

Compound (17) was dissolved in absolute ethanol (120 ml) and cooled to 0° C. Sodium borohydride (1.05g) dissolved in absolute ethanol (60 ml) was added dropwise over 10 minutes to the stirred steroid solution, and the solution was allowed to stir 15 minutes more. Excess $NaBH_4$ was decomposed by dropwise addition of acetic acid. The solvent was evaporated, and the product was isolated with ethyl acetate and then crystallized from acetone-hexane to give (13, 5.56g) (95.3%).mp 113°-115° C; $\nu_{max}$3400, 1740 cm.$^{-1}$ ANAL. Calcd for $C_{23}H_{36}O_4S$: C., 67.61; H., 8.88; O., 15.66; S., 7.85. Found: C., 67.34; H., 9.01.

EXAMPLE IV

17β-Hydroxyandrost-4-en-3-one-15β-methyl (propionate) thioether (19)

Compound (18) (.600g) was dissolved in cyclohexane (13 ml). Toluene (100 ml) was added, then 40 ml toluene was distilled off to remove traces of moisture by azeotropic distillation, and the solution was cooled. Aluminum tertbutoxide (2.47g) was added and the mixture was refluxed 5 hours, then cooled. Excess t-butoxide was decomposed using iced HCl. The mixture was extracted with ether, washed with ice-water, and steam-distilled to remove cyclohexane and toluene. The gummy residue was cooled and extracted again with ethyl acetate to give a mixture of 17-hydroxy and 17-keto compounds (.49g). These compounds were separated using a Girard separation which isolated the ketonic portions (0.242g). The ketonic portion was chromatographed on silica gel to give pure product (19, 0.116g) (19.4%) $\nu_{max}$3440, 1740, 1680 cm.$^{-1}$; $\lambda_{max}$(MeOH) 240 nm; δ 1.06 (s.—CH$_3$) 1.23 (S.—CH$_3$) 3.74 (S.—OCH$_3$)ppm.

EXAMPLE V

17β-Hydroxyandrost-4-en-3-one-15β-carboxyethyl thioether (20)

The methyl ester (19, 0.689g) was dissolved in methanolic KOH solution (1.0 M KOH in methanol, 35 ml) and allowed to stir under N$_2$ overnight. The methanol was evaporated, ethyl acetate and water were added, and the mixture separated into neutral and acidic fractions. The acidic fraction was cooled, brought to pH2 with HCl, extracted again with ethyl acetate, and crystallized from acetone-ether to give the final product (20, 0.39g)(58.6%)mp 202°-204° C.; $\nu_{max}$3400, 1720, 1650 cm.$^{-1}$; $\lambda_{max}$(MeOH) 241 nm ($\epsilon$, 16,463).

ANAL. Calcd for C$_{22}$H$_{32}$O$_4$S: C., 67.31, H., 8.22; O., 16.30; S., 8.17. Found: C., 67.41; H., 8.24.

EXAMPLE VI

The methyl ester (16) (0.475g) is dissolved in methanol and 1.03 ml of 5% NaOH is added thereto. After 21 hours, the solvent is evaporated and the mixture dissolved in water and ethyl acetate. The aqueous phase is recovered, acidified to pH2 with hydrochloric acid, followed by extraction with ethyl acetate and a water wash. After drying and evaporation of solvent, there is obtained 0.234g of 3β-Hydroxyandrost-5-en-17-one-15α-carboxyethyl thioether which is converted to the corresponding methyl ester by reaction with diazomethane in methanol.

The 15α forms of compounds 18, 19 and 20 are produced as described in Examples III, IV and V using the product of Example VI as a starting material.

Compounds 20 and 20A of the present invention are steroid haptens, and when linked to a suitable immunological carrier, preferably a protein, such conjugates can be employed to elicit antibodies which are specific to testosterone and 5α-dihydrotestosterone, respectively. The term "immunological carrier" means a material which has the property of eliciting an immunological response in a host animal.

As representative examples of suitable immunological carriers, there may be mentioned proteins, natural or synthetic polymers, such as, polypeptides; e.g., polylysine; polysaccharides; specific representative examples are bovine serum albumin (BSA), human serum albumin, poly (L-Lysine), ovalbumin, alpha-, beta and gamma globulins, thryroglobulin, and the like.

The compound of the present invention is conjugated to the protein by use of a suitable chemical coupling agent. As representative examples of coupling agents, there may be mentioned: carbodiimide; mixed anhydrides and the like. The use of coupling agents for conjugating a hapten to an immunological carrier is well known in the art, and no further details in this respect are deemed necessary for an understanding of the invention.

The antibody is elicited by injecting the conjugate into a host animal by procedures known in the art. In general, such a procedure involves injecting the conjugate (immunogen) into a host animal repeatedly over a period of time, collecting the serum and precipitating the antibody with a neutral salt. Suitable host animals include mammals, such as rabbits, horses, goats, guinea pigs, rats, cows, sheep, etc.

The invention will be further described with respect to the following examples for producing a conjugate and eliciting an antibody by use of the conjugate using testosterone-15β- carboxyethyl thioether. It is to be understood that the procedure is also applicable to the 15α form and to the related 5α-dihydrotestosterone derivative.

EXAMPLE VII

I. Formation of the Anhydride 1. 300 mg. of testosterone-15β-carboxyethyl thioether was dissolved in 10cc of anhydrous dioxane and a 3 molar excess of tri-n-butylamine (0.30 ml) was added with mixing.

2. The above mixture was cooled to 11° C in a water bath and a 3 molar excess of isobutyl chloroformate (0.546 ml) was added with vigorous mixing.

3. The formation of the mixed anhydride was allowed to proceed for about 60 minutes at 11° C with occasional shaking of the stoppered reaction mixture.

4. The reaction mixture was then blown down with nitrogen and taken to dryness under high vacuum.

II. Coupling Procedure 1. 1.070 grams of BSA was dissolved in 39 ml of distilled water and the pH brought to 8.5 with NaOH. 39 ml of dioxane was then added with the pH maintained between 8.3 – 8.5.

2. The mixed anhydride was brought back into solution with 10cc of dioxane and slowly added to the cooled (ice bath) solution of BSA at pH 8.5. At this time, pH was maintained at 8.5.

3. After stirring for 4 hours at ice bath temperature and pH 8.5., the pH was adjusted to 7.0 and the dioxane solution dialyzed against running distilled water at 2°-4° C overnight.

III. Isolation of the Conjugate

1. The dialysate (175ml) was brought to 25% (v/v) with acetone by the addition of 58 ml for a total volume of 233 ml.

2. The pH of the dialysate before acetone was 4.8 and 5.1 after addition of the acetone. The pH was brought to 8.5 and the somewhat clear solution was stirred for 30 minutes at 0° C.

3. The point of maximum precipitation was found to be pH 4.3. The solution was kept at this pH for 15 minutes with the precipitate collected by refrigerated centrifugation.

4. The precipitate was then resuspended and resolubilized in distilled water and brought to 25% (v/v) with acetone as above. The precipitate was washed and reprecipitated two more times using the same procedure.

5. The final washed conjugate was solubilized at pH 7.0 in distilled water and dialyzed overnight using the same procedure as above. The final dialysate was frozen and then dried by lyophylization.

6. A total of 1.0 gram of the conjugate was collected for a 77% recovery.

IV. Eliciting Antibody

The steroid conjugate (testosterone-15β-carboxyethyl thioether-BSA was dissolved in isotonic saline at a concentration of 2 mg/ml and mixed with Freund's complete adjuvant (1:1) for a final dilution of 1 mg/ml. The primary injection (2mg) was divided into four equal portions and injected intramuscularly into each thigh and below each shoulder blade of five male New Zealand White rabbits (4 months old). Intramuscular injections of 0.5 mg into each thigh was repeated 7, 14 and 21 days after the initial injection, and every 30 days thereafter. Plasma was collected 14 days after the third booster injection and every 30 days thereafter.

The haptens of the present invention are particularly advantageous in that such haptens can be employed for producing antibodies which are highly specific to testosterone and 5α-dihydrotestosterone, respectively. Thus, for example, the anti-serum produced by use of the hapten, testosterone-15β-carboxyethyl thioether showed no cross-reaction with closely related compounds and, accordingly, the anti-serum developed by use of such hapten is of considerable importance in measuring testosterone levels in animal fluids, and in particular, in female plasma samples.

The respective antibodies can be employed for measuring testosterone and 5α-dihydrotestosterone levels in a fluid sample by the procedure of radioimmunoassay, a procedure generally known in the art. In accordance with such procedure, labeled steroid and unlabeled steroid present in a sample compete for binding sites on the antibody, and as a result of the competition, the ratio of bound labeled steroid to free labeled steroid diminishes as the concentration of unlabeled steroid in the sample increases. The amount of unlabeled steroid in a sample is obtained by comparing the inhibition observed with that produced by known amounts of unlabeled steroid, as presented in a standard curve.

The following is a representative protocol for preparing standard curves for a radioimmunoassay, and as known in the art, an identical procedure is used for the actual assay. In the protocol, the labeled steroid is either tritiated testosterone or tritiated 5α-dihydrotestosterone and the anti-serum is the antibody elicited by using the corresponding immunogen of the present invention. It is understood that steroids labeled with other radioactive nuclides may also be used.

EXAMPLE VIII

Liquid Phase

Standards are prepared from stock solutions of unlabeled steroid in absolute ethanol (100 ng/ml.). Two working standard solutions containing 1 ng/ml and 4 ng/ml are prepared in sodium phosphate assay buffer (0.1 M, pH-7, 0.9% NaCl, 0.1% sodium azide). The tritiated labeled steroid is prepared in assay buffer at a concentration of 100 picograms/ml. The antiserum is prepared in BSA-assay buffer (1 gm BSA/1000 ml sodium phosphate buffer) at a concentration of one-fifth of the final working dilution (titer). The standard curve is established by setting up duplicate 3 ml centrifuge tubes containing 0, 50, 100, 250, 500, 1,000, and 2,000 picograms of the steroid in a total volume of 0.5 ml of assay buffer. After addition of 0.5 ml of the labeled steroid and 0.25 ml of the antisera, all standard tubes are mixed on a Vortex and incubated at 4° C overnight. After addition of 0.2ml of cold gamma globulin dextran coated charcoal (1 g charcoal, 0.1 g dextran, 0.2 g gamma globulin, 200 ml deionized water), each tube is again mixed and returned to the cold room for 20 minutes. After centrigufation at 2,500 rpm for 6 minutes, 0.2 ml of each supernatant is aliquoted into a counting vial. Then 15 ml of scintillation medium (4 g PPO, 50 mg dimethyl-POPOP, 50 ml BBS-3, 1,000 ml toluene) is added to each vial. The samples are counted in a Packard Liquid Scintillation Counter Model 3320.

Solid Phase

A mixture, to be used in the solid-phase curve, of the covalently bound antibody and the labeled antigen is preincubated for 24 hours prior to its use. A single ml aliquot of this solution, at a final working dilution of 1:3000 is added to each tube. Varying amounts of the unlabeled steroid in a total volume of 0.5 ml is added to each tube as in the liquid phase. The tubes are mixed on a Vortex mixer, allowed to stand at room temperature for 1 hour, mixed again, and then allowed to stand for an additional hour. After centrifugation at 2,500 rpm for 6 minutes, 0.2 ml of the supernatant, representing the free fraction, is aliquoted and counted as above.

Numerous modifications and variations of the present invention are possible in light of the above teachings and, therefore, within the scope of the appended claims, the invention may be practiced otherwise than as particularly described.

What is claimed is:

1. An immunogen comprising:
   an immunological carrier having conjugated thereto by a chemical coupling agent a compound selected from the group consisting of compounds represented by the formula:

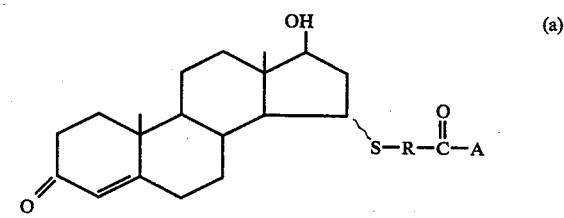

(a)

wherein R is an alkyl group of from 1 to 6 carbon atoms A is selected from the group consisting of —OH, —OM wherein M is an alkali metal barium, calcium, or strontium, and OY wherein Y is an alkyl group of from 1 to 6 carbon atoms; and

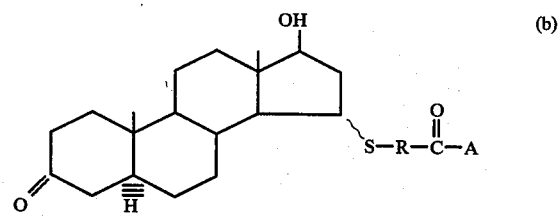

(b)

wherein R and A are as defined above.

2. The immunogen of claim 1 wherein the compound has structural formula (a).

3. The immunogen of claim 2 wherein the compound is in the 15β form.

4. The immunogen of claim 3 wherein A is —OH.

5. The immunogen of claim 4 wherein R is an alkyl group having 2 carbon atoms.

6. The immunogen of claim 1 wherein the compound has structural formula (b).

7. The immunogen of claim 6 wherein the compound is in the 15β form.

8. The immunogen of claim 7 wherein A is —OH.

9. The immunogen of claim 8 wherein R is an alkyl group having 2 carbon atoms.

10. The antibody produced by injecting the immunogen of claim 2 into a host animal.

11. The antibody produced by injecting the immunogen of claim 3 into a host animal.

12. The antibody produced by injecting the immunogen of claim 4 into a host animal.

13. The antibody produced by injecting the immunogen of claim 5 into a host animal.

14. The antibody produced by injecting the immunogen of claim 6 into a host animal.

15. The antibody produced by injecting the immunogen of claim 7 into a host animal.

16. The antibody produced by injecting the immunogen of claim 8 into a host animal.

17. The antibody produced by injecting the immunogen of claim 9 into a host animal.

18. In the radioimmunoassay of testosterone in a sample employing radiolabeled testosterone and an antibody for binding testosterone and radiolabeled testosterone, the improvement comprising:

employing the antibody of claim 13 as said antibody.

19. In the radioimmunoassay of 5-α-dihydrotestosterone in a sample employing radiolabeled 5-α-dihydrotestosterone and an antibody for binding 5-α-dihydrotestosterone and radiolabeled 5-α-dihydrotestosterone the improvement comprising:

employing the antibody of claim 17 as said antibody.

* * * * *